(12) United States Patent
Ahn et al.

(10) Patent No.: US 8,654,920 B2
(45) Date of Patent: Feb. 18, 2014

(54) SYSTEM FOR DETECTING PIN HOLE OF FUEL CELL STACK PARTS

(75) Inventors: Sang Yeoul Ahn, Seoul (KR); Keun Je Lee, Gyeonggi-do (KR); Byung Ki Ahn, Gyeonggi-do (KR); Sung Keun Lee, Gyeonggi-do (KR); Tae Won Lim, Seoul (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 300 days.

(21) Appl. No.: 13/110,272

(22) Filed: May 18, 2011

(65) Prior Publication Data

US 2012/0140880 A1 Jun. 7, 2012

(30) Foreign Application Priority Data

Dec. 2, 2010 (KR) .......................... 10-2010-0121766

(51) Int. Cl.
*G01N 23/02* (2006.01)
(52) U.S. Cl.
USPC ............................................................ 378/58
(58) Field of Classification Search
USPC ....................... 378/58–60, 62, 98.7
See application file for complete search history.

(56) References Cited

U.S. PATENT DOCUMENTS

| 7,274,770 | B2* | 9/2007 | Nederpelt ........................ 378/97 |
| 7,499,521 | B2* | 3/2009 | Wang et al. ...................... 378/43 |
| 7,522,700 | B2* | 4/2009 | Bavendiek et al. ............. 378/58 |
| 2008/0165924 | A1 | 7/2008 | Wang et al. |
| 2011/0122991 | A1* | 5/2011 | Ahn et al. ........................ 378/10 |

FOREIGN PATENT DOCUMENTS

| JP | 06018445 | | 1/1994 |
| JP | 2004325346 | A | 11/2004 |
| JP | 2005134218 | A | 5/2005 |
| JP | 2005-522237 | A | 7/2005 |
| JP | 2009-058528 | A | 3/2009 |
| JP | 2010169528 | A | 8/2010 |
| JP | 2010-217098 | A | 9/2010 |
| KR | 10-2007-0068170 | A | 6/2007 |
| KR | 10-2008-0030800 | | 4/2008 |
| KR | 10-2010-0075295 | | 7/2010 |

* cited by examiner

*Primary Examiner* — Jurie Yun
(74) *Attorney, Agent, or Firm* — Edwards Wildman Palmer LLP; Peter F. Corless

(57) ABSTRACT

The present invention relates to a device and a method for detecting a pin hole in a part of a fuel cell stack part to accurately detect the presence of pin holes of stack parts thereby ensuring quality of a fuel cell stack. That is, the present invention provides a system for detecting a pin hole in parts of a fuel cell stack that allows for quality assurance of the fuel cell stack and prevents defective parts from being used, by examining each fuel stack part, which largely influence the quality of the fuel cell stack, using an X-ray device and a vision system, in order to determine the presence of a pin hole in the parts, and a method thereof.

9 Claims, 4 Drawing Sheets ian Patent Application No. 10-2010-0121766 filed
SYSTEM FOR DETECTING PIN HOLE OF FUEL CELL STACK PARTS

CROSS-REFERENCE TO RELATED APPLICATION

This application claims under 35 U.S.C. §119(a) the benefit of Korean Patent Application No. 10-2010-0121766 filed Dec. 2, 2010, the entire contents of which are incorporated herein by reference.

BACKGROUND (a) Technical Field

The present invention relates to a system for detecting a pin hole in a fuel cell stack part. More particularly, it relates to a device and a method for accurately detecting the presence of pin holes in fuel cell stack parts for ensuring quality of the fuel cell stack.

(b) Background Art

A fuel cell stack is typically manufactured by alternately stacking hundreds or more of five-layered membrane-electrode assemblies having a gas diffusion layer on both sides of three-layered membrane-electrode assemblies and metal (or graphite) separators.

In particular, the membrane electrode assemblies (MEA) and gas diffusion layers are bonded together to form a five-layered structure, before the stack is manufactured, to improve productivity of the fuel cell stack. Here, the carbon fibers constituting the gas diffusion layers may bore or permeate the polymer electrolyte membrane layers of the membrane electrode assemblies (MEA) such that pin holes may be formed in the above bored or permeated portions. In the case of a separator, it is highly likely that pin holes are formed during a pressing process for the manufacture of a single product.

Further, in the fuel cell stack, when deterioration of the entire polymer electrolyte membranes is not uniform, pin holes may be formed in deteriorated portions, thereby damaging the corresponding cells and terminating the lifespan of the entire stack.

Therefore, when a part with pin holes is used in manufacturing a fuel cell stack, the output performance and durability of the stack are considerably influenced. Accordingly, when a fuel cell vehicle equipped with the stack travels, a pin hole is formed in any one of the hundreds of membrane electrode assemblies and/or separators, and the operation of the vehicle is shut down. Therefore, it is essential to check for the presence of pin holes in each part before the manufacture and assembly of the fuel cell stack.

As an example of a conventional technique for examining pin holes in the related art, Korean Patent No. 10-0053351 discloses an optical apparatus for the detection of holes, in which a photoelectric light receiver is disposed on the same side as a laser scanner and receives light reflected from a scan line. A second laser scanner is also disposed in a limited space (i.e., A) in front of a web from a first laser scanner at the opposite side to the web and scans the other side of the web in the limited space A, using a scan line parallel with a first scan line. Another linear photoelectric light receiver extends in parallel with a second scan line and sends an electric signal to an electronic process circuit after receiving light reflected from the second scan line. Electric signals transmitted to the electronic process circuit from the two photoelectric light receivers come in connection with an intermediate storage device which is stores a first received signal. Then a pin hole signal is transmitted, when the same signals are generated from the same positions of the webs of both light receivers.

However, the above apparatus cannot measure the parts of a multi-layered fuel stack because it can only be applied to single-layered webs. Thus, it is limited when measuring the parts with a laser scanner and a light receiver, because the shapes of pin holes generated in a porous three-layered or five-layered MEA or separator, which has a multi-layered structure as a part of a fuel cell stack, do not have linearity.

Further, it is not possible to apply the above apparatus to the parts of a fuel cell stack by conveying a roll type object, such that MEAs (three-layered or five-layered) and separators which are the parts of the fuel cell stack cannot be continuously conveyed through bias rollers, because they need a certain degree of flatness in a quadrangular sheet type, and accordingly, the parts of the fuel cell are destroyed by rolling.

Another example of related art appears in Korean Patent No. 10-0878400 which discloses a pin hole detector, in which light passing through a pin hole, in the z-axis direction, is combined with a photo detector. Since the traveling direction of noise light, except for the light passing through the pin hole is inclined with respect to z-axis, a combination of the noise light with the photo detector is limited by a first and second optical means that limits the incident angle.

However, the apparatus cannot measure the parts of a multi-layered fuel stack because it can only be applied to metal or resin film. That is, it is limited in measuring the parts with an optical scanner and a light receiver, because the shapes of pin holes generated in a porous three-layered or five-layered MEA or separator, which has a multi-layered structure as a part of a fuel cell stack, do not have any linearity.

As another example, Korean Patent Application No. 10-2002-0084521 discloses a pin hole detector that detects a pin hole in a thin plate material, such as a steel plate, and includes a laser light source that generates a laser line beam with a single wavelength, a first cylindrical lens that converts a line beam from the laser light source into parallel light, a second cylindrical lens that collects the parallel light, an APD (Avalanche Photo Diode) sensor that is disposed at the focus of the second cylindrical lens, and a signal processor that determines the presence of a pin hole based on the output from the APD sensor.

However, this apparatus can only be applied to single layered metals but not to parts such as a multi-layered fuel cell stack. The pin holes generated in a porous three-layered or five-layered MEA or separator, which has a multi-layered structure as a part of a fuel cell stack, do not always have linearity, and thus the measurement using the laser line beam and the APD sensor is limited.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

The present invention provides a system for detecting a pin hole in fuel cell stack (i.e., its elements or parts) that allows for an ensured quality of the fuel cell stack and prevents defective parts from being used, by examining each stack part, (e.g., the parts that largely influence the quality of the fuel cell stack), using an X-ray device and a vision system, in order to determine the presence of pin holes in each the parts.

In one aspect, the present invention provides a system for detecting a pin hole in one or more fuel cell stack parts. In particular, the system includes an X-ray device and a vision computing system. The X-ray device photographs the parts of a fuel cell stack. An image processor then produces an image signal outputted from the X-ray device. This produced image signal is then sent/transmitted to a vision computer to determine whether the corresponding parts are normal or defective by selectively receiving and analyzing the image signal imaged by the image processor. The vision computing system then accumulates and calculates the image determination results to manage quality data related to the fuel cell stack, and transmits output instructions for photographing control to the X-ray device.

Advantageously, unlike the existing optical detection for finding pin holes which are limited in their ability to detect the presence of a pin hole in a membrane electrode assembly and a separator in a fuel cell stack, the present invention is able to accurately detect the presence of a pin hole in each part, via a non-destructive test conducted via an X-ray and a vision system and it also is able to more accurately examine a pin hole through the use of an image. Since X-ray photographing and digital image analysis of signals takes less than one second in the present invention, the present invention is able to realize a high detection speed, which takes less than 10 seconds to detect one part, including conveyance time for each part.

BRIEF DESCRIPTION OF THE DRAWINGS

The above and other features of the present invention will now be described in detail with reference to certain exemplary embodiments thereof illustrated the accompanying drawings which are given hereinafter by way of illustration only, and thus are not limitative of the present invention, and wherein.

Figure 1:
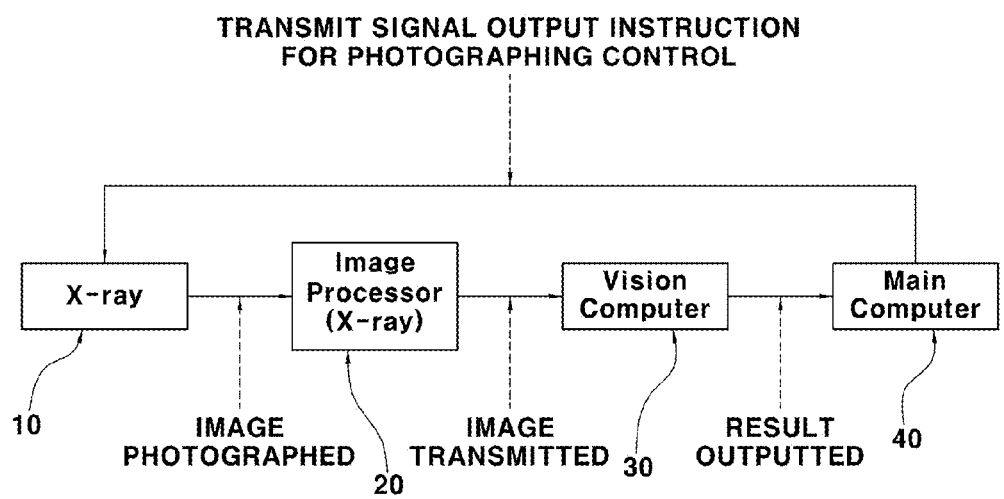
FIG. 1 is a control block diagram illustrating a system for detecting a pin hole in fuel cell stack parts according to an illustrative embodiment of the present invention.
Figure 2:
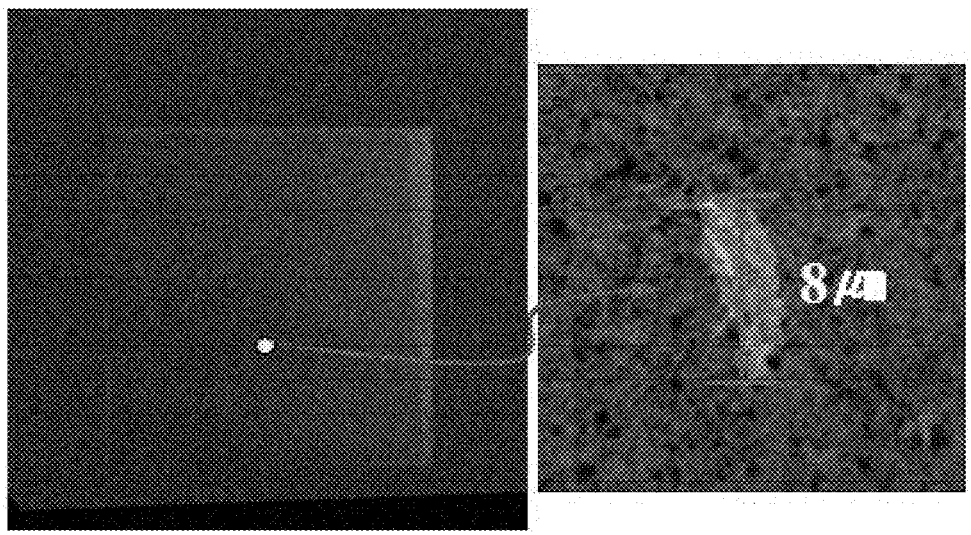
FIG. 2 is an image of a pin hole observed by a test of the present invention.

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

Examples

The following examples illustrate the invention and are not intended to limit the same.

Hereinafter, illustrative embodiments of the present invention will be described in detail with reference to the accompanying drawings.

The present invention provides a detection technique which utilizes an X-ray device and a vision system in combination, in order to detect the presence of pin holes in parts of a fuel cell stack (particularly, a polymer electrolyte membrane, a catalyst layer, and a gas diffusion layer that constitute a five-layered membrane electrode assembly).

In this configuration, a system for detecting a pin hole of the present invention, as shown in FIG. 1, includes: an X-ray device 10, an image processing unit 20 and a vision computing system 30. The X-ray device 10 photographs the parts of a fuel cell stack (particularly, a five-layered membrane electrode assembly) and the image processor 20 produces an image signal outputted from the X-ray device 10. The vision computing system (computer) 30 determines whether the corresponding parts are in normal condition or are defective by selectively receiving and analyzing the image signal imaged by the image processor 20. A separate main computer 49 then accumulates and calculates the image determination results upon receiving the results from the vision computing system 30 to manage data related to the quality of the parts of the fuel cell stack. Output instructions for photographing control are then transmitted to the X-ray device 10, in which the vision computer 30, not the main computer, may also transmit the output instructions for photographing control of the X-ray device 10.

Figure 3:
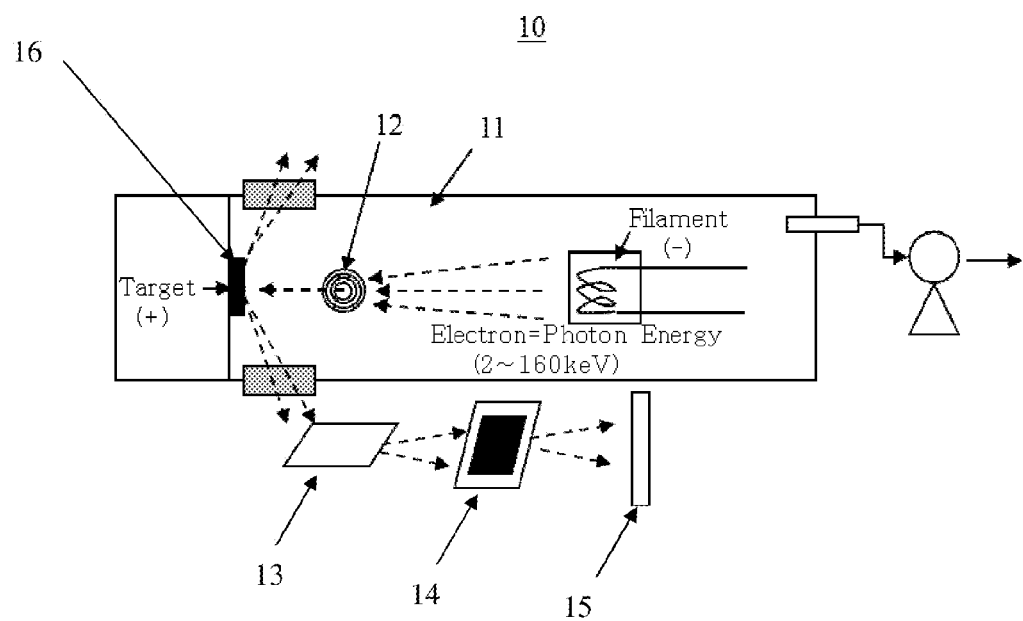
FIG. 3 is a schematic diagram of the X-Ray Device of FIG. 1.

As shown in FIG. 3, the X-ray device 10 is composed of an X-ray source, an energy filter 13 that can improve clearness of the image by removing noises when photographing the parts 14 of the fuel cell, and a high resolution image detector 15 that detects the photographed image in an image signal.

The X-ray source may uses photon energy in the range of, e.g., about 2~160 keV and a window (e.g., a target window) made of either Rh, Cr, Cu, or W is used for a target where the parts of the fuel cell are seated. Illustratively, in some embodiments of the present invention the window is made of Be having a low absorption rate in the light X-ray region within, e.g., about 5~60 keV.

In this configuration in FIG. 3, the X-ray photography is performed by keeping the vacuum level at, e.g., about $10^{-7}$ torr or less and adjusting the minimum focus to about 1.0 μm or more at 16, in a radiating pipe 11 (the X-ray source), as a photographing condition of the X-ray device 10, in order to minimize absorption and dispersion by air.

The high resolution image detector may, e.g., have about 1 □m or more of pixel resolution and can operate in a phase contrast mode with a phase ring in a back focal plane of a zone plate 12 included in the high resolution image detector 15, so that it is easier to control the contrast of the image transmitting the X-ray.

Figure 4:
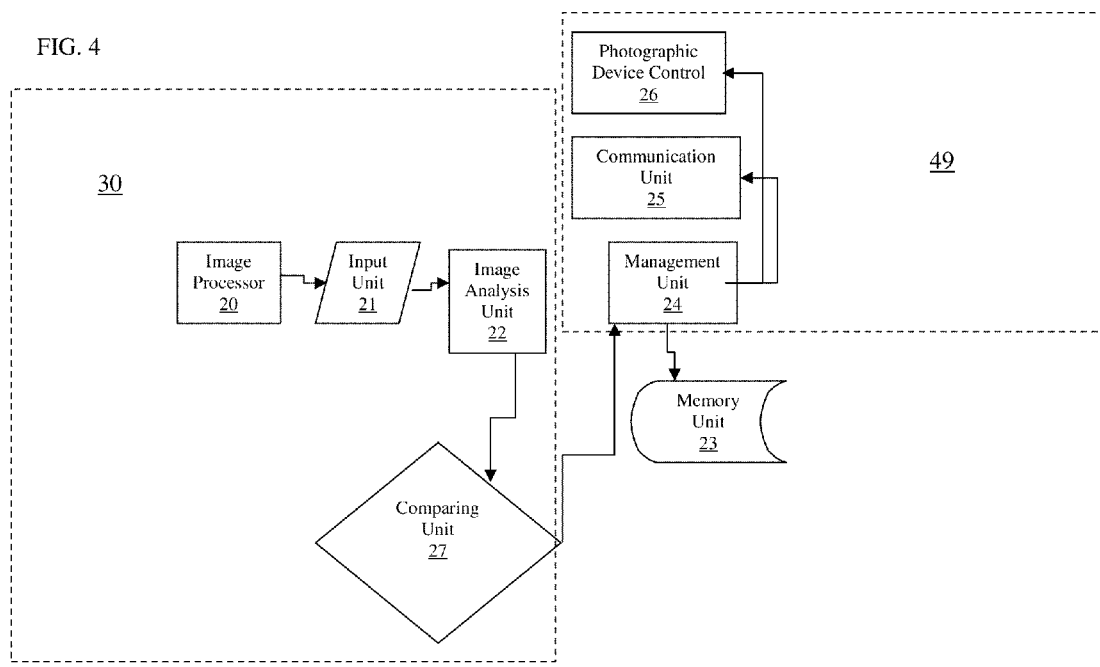
FIG. 4 is a schematic diagram of the computational system of the exemplary embodiment of the present invention.

Meanwhile, as shown in FIG. 4, the vision computing system 30 includes a memory unit 23 that stores reference information for the normal state of the parts of the fuel cell stack, an input unit 21 where the image signals acquired by the image processor 20 are inputted, and image analyzing unit 22 that analyzes digital image signals inputted through the input unit 21. The vision computing system 30 may also embody a comparing unit 27 that determines normality or defect by comparing the image analysis result from the image analyzing unit with the reference information stored in the memory unit 23, and a communication unit that transmits the result determined by the comparing unit 27 to the main computer. In particular, the image analyzing unit 22 that analyzes the digital image signals may also be configured to analyze contrast, brightness, pattern match, contour match, position, width, and counting.

Further, the main computer 49 includes an input unit where the results determined by the comparing unit of the vision computing system 30 are inputted, a managing unit 24 that manages quality data of the parts in the stack by accumulating and calculating the image determination results, and a photographic device control unit 26 that outputs operation signals to the X-ray device 10.

Hereinafter, an embodiment of detecting a pin hole of the parts of a fuel cell, using a system for detecting a pin hole of the present invention is described.

First, there is provided a five-layered membrane-electrode assembly (MEA) for a fuel cell, which includes a nafion-based fluorine polymer electrolyte membrane, a Pt/C catalyst bonded to both sides of the above membrane, and a gas diffusion layer (GDL) made of carbon paper bonded to the catalyst layer.

In a process of manufacturing the five-layered membrane-electrode assembly, the five-layered membrane-electrode assembly is manufactured by randomly forming a pin hole of, e.g., several micrometers, in the membrane (MEA) by using a laser; forming a catalyst on both sides of the membrane with the pin hole; and then hot-pressing a gas diffusion layer (GDL) on the outer surface of the catalyst.

Next, the five-layered membrane-electrode assembly (MEA) for a fuel cell, which is configured as described above, is X-rayed by an X-ray device 10 having an X-ray source (e.g., 50 keV with target made of W).

In the illustrative embodiment of the present invention, when an image signal is acquired by the X-ray device 10, it is then imaged by the image processor 20 and the image signal imaged by the image processor 20 is analyzed by the vision computing system 30, thereby determining whether the five-layered MEA part is normal or has a defect. The determined results are then stored in the main computer 49 to manage quality data of the parts of the stack.

Therefore, as a result of determining a defect in the five-layered MEA by the vision computer 30, as seen from the image in FIG. 1, it can be seen that a pin hole of, e.g., about 8 µm created in an electrolyte membrane in the five-layered MEA of the fuel cell, through the X-ray device.

Furthermore, the present invention may be embodied as computer readable media on a computer readable medium containing executable program instructions executed by a processor. Examples of the computer readable mediums include, but are not limited to, ROM, RAM, compact disc (CD)-ROMs, magnetic tapes, floppy disks, and optical data storage devices. The computer readable recording medium can also be distributed in network coupled computer systems so that the computer readable media is stored and executed in a distributed fashion.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. A system for detecting a pin hole in fuel cell stack parts, comprising:
   an X-ray device that photographs the fuel cell stack parts to output a photograph signal;
   an image processor that produces, as an image signal, the photograph signal outputted from the X-ray device;
   a vision computing system that
      (i) determines whether corresponding fuel cell stack parts are normal or defective by receiving and analyzing the image signal from the image processor; and
   a separate main computer that:
      (ii) accumulates and calculates an image determination result to manage quality data of the fuel cell stack parts by receiving the determined result from the vision computing system, and
      (iii) transmits output instructions for photographing control to the X-ray device.

2. The system of claim 1, wherein the X-ray device includes an X-ray source, an energy filter that improves clearness of an image by removing noise in photographing, and a high resolution image detector that detects the photographed signal in an image signal.

3. The system of claim 2, wherein the X-ray source uses photon energy in the range of 2~160 keV, a window made of one of a group consisting of Rh, Cr, Cu, and W is used as a target, and a window made of Be having a low absorption rate is used in the light X-ray region employing photon energy in the range of 5~60 keV.

4. The system of claim 2, wherein the X-ray photography is performed by keeping a vacuum level of a radiating pipe of the X-ray source at 10−7 torr or less and adjusting a minimum focus at 1.0 µm or more, in the radiating pipe of the X-ray source, in order to minimize absorption and dispersion by air.

5. The system of claim 1, wherein the vision computing system includes:
   a memory unit that stores reference information for the normal state of the parts of the fuel cell stack;
   an input unit where the image signals produced by the image processor are inputted, and an image analyzing unit that analyzes the image signals inputted through the input unit;
   a comparing unit that determines normality or defect by comparing an image analysis result from the image analyzing unit with the reference information stored in the memory unit; and
   a communication unit that transmits a result determined by the comparing unit to the separate main computer.

6. The system of claim 5, wherein the image analyzing unit that analyzes the image signals from the vision computing system is configured to analyze contrast, brightness, pattern match, contour match, position, width, and counting the fuel cell stack parts.

7. The system of claim 1, wherein the main computer includes:
   an input unit where the results determined by a comparing unit of the vision computing system are inputted;
   a managing unit that manages quality data of the parts in the stack by accumulating and calculating the image determination result; and
   a photographic device control unit that outputs operation signals to the X-ray device.

8. A method for detecting a pin hole in fuel cell stack parts, comprising:
   photographing by an X-ray device one or more parts of a fuel cell stack to output a photograph signal;
   producing by an image processor, as an image signal, the photograph signal outputted from the X-ray device;

determining, by a vision computing system, whether corresponding parts of the fuel cell stack are normal or defective by receiving and analyzing the image signal from the image processor, accumulating and calculating by a separate main computer, an image determination result to manage quality data of the fuel cell stack parts, and transmitting by the separate main computer output instructions for photographing control to the X-ray device.

9. A non-transitory computer readable medium containing executable program instructions executed by a processor, comprising:

program instructions that photograph via an X-ray device one or more parts of a fuel cell stack to output a photograph signal;

program instructions that produce by an image processor as an image signal, the photograph signal outputted from the X-ray device;

program instructions that determine, by a vision computing system, whether corresponding parts of the fuel cell stack are normal or defective by selectively receiving and analyzing the image signal from the image processor, program instructions that accumulate and calculate by the vision computing system an image determination result to manage quality data of the fuel cell stack parts, and program instructions that transmit output instructions for photographing control to the X-ray device.

\* \* \* \* \*